United States Patent [19]

Gillman et al.

[11] 4,026,830

[45] May 31, 1977

[54] POLY[TANTALUM PHOSPHINATES]

[75] Inventors: Hyman D. Gillman, Phoenixville; James P. King, Lansdale, both of Pa.

[73] Assignee: The United States of America as represented by the Secretary of the Navy, Washington, D.C.

[22] Filed: Aug. 18, 1975

[21] Appl. No.: 605,796

[52] U.S. Cl. .......................... 260/2 P; 260/429 R; 260/47 R
[51] Int. Cl.² ...................... C07F 9/00; C08G 79/04
[58] Field of Search .............. 260/429 R, 2 M, 2 P; 252/431 P

[56] References Cited

UNITED STATES PATENTS

| 3,255,125 | 6/1966 | Block et al. | 260/429 R X |
| 3,275,574 | 9/1966 | Saraceno | 260/429 R X |
| 3,444,103 | 5/1969 | Maguire | 260/429 R X |

OTHER PUBLICATIONS

Chemical Abstracts, 68, 35401n (1968).
Chemical Abstracts, 73, 41318k (1970).

Primary Examiner—Helen M. S. Sneed
Attorney, Agent, or Firm—R. S. Sciascia; Philip Schneider; Thomas McDonnell

[57] ABSTRACT

Tantalum phosphinates of the general formula: [Ta(OPRR'O)$_p$(Z)$_{5-p}$]$_n$ wherein $1 \leq p \leq 3$; R and R' are aryl groups; Z may be a halo, alkoxy, or aryloxy group or a mixture thereof; and n may be any number. The preparation thereof is based on the reaction of a tantalum pentavalent compound (TaZ$_5$) with a phosphinic acid (RR'P(O)OH) in a dry inert solvent at reflux temperature. Such compounds are useful in high temperature laminates as fillers. Oxide hydrates of these compounds may be prepared by hydrolysis and are similarly useful in high temperature laminates as fillers.

5 Claims, No Drawings

POLY[TANTALUM PHOSPHINATES]

BACKGROUND OF THE INVENTION

The invention relates generally to the preparation of inorganic coordination polymers and in particular to the preparation of tantalum phosphinates.

Phosphinate ligands have been found to act as bridging groups in a variety of complexes with numerous metals. However, to date, such has not been found to occur with third row transition metals. Some success has been reported with phosphonates and a few third row transition metals, but the variety and quality of the products have been limited.

Many special purpose resins have a major drawback. They are extremely expensive. Techniques which are used to reduce the high cost inherent with their use are to form laminates with less expensive resins or use less expensive resins as fillers. In developing these resins, a number of properties are sought besides lower costs. First the materials must be compatible with a large variety of other materials. These fillers must be able to form a strong bond with the other resins nor be detrimental to the physical properties of these resins. Further these cheaper fillers must have a high structural strength and temperature stability. Of course it is desirable if the cheaper material improves some of the properties of the expensive resin, e.g. adhesion, abrasion resistance, or fire retardancy.

SUMMARY OF THE INVENTION

It is therefore an object of the invention to provide novel tantalum phosphinates efficiently and cheaply.

A further object of this invention is to provide a new class of high temperature laminate fillers.

Another object is to provide inexpensive resins which are compatible with a large variety of other resins.

Also an object of this invention is to provide a resin which has a high temperature stability, abrasion resistance, and adhesion.

These and other objects are achieved by (1) tantalum phosphinates of the general formula: $[Ta(OPRR'O)_pZ_{5-p}]_n$ wherein $1 \leq p \leq 3$; R and R' are phenyl groups or phenyl derivatives in which the benzene ring has not been inactivated by electron withdrawing substituents or mixtures thereof; Z is a chloride, bromide, an alkoxy group which is not so large as to detrimentally dilute the effect of tantalum phosphinate, an aryloxy group which is not so bulky as to cause stearic hindrance, or mixtures thereof, and $n$ may be any value; and (2) by oxide hydrates thereof having the general formula: $[Ta[OPRR'0]_xO_y\cdot zH_2O]_n$ wherein $1 \leq x \leq 3, y = (5-x/2), 0.5 \leq z \leq 2.0$, in any value, and R and R' are as before.

DETAILED DESCRIPTION OF THE INVENTION

All of the tantalum phosphinates may be prepared according to the following mechanism:

$$TaZ_5 + pRR'P(O)OH \rightarrow 1/n\ [Ta(OPRR'O)_pZ_{(5-p)}]_n + pHZ$$

wherein Z is a halide, alkoxide, or aryloxide. The two reactants are admixed together in a dry inert solvent such as benzene, toluene, xylene, chlorobenzene, or dichlorobenzene. The solution is then refluxed until the reaction is complete as determined by a continuing analysis of one of the reactants in the reaction solution by, for example, infrared analysis.

In order to obtain the tris phosphinate, a solvent with a boiling point above 100° C such as toluene with a boiling point of 110° C is used along with the correct stoichimetric amount of the phosphinic acid. For the mono and bis forms, any solvent may be used and the product is controlled by the amount of the phosphinic acid used. Only a stoichiometric amount is to be used.

Preferably the reactants are at least reagent grade.

A tantalum penta-valent compound is one of the reactants. The tantalum penta-halides which can be used are the chloride and bromide. Preferably the alkoxy group in the tantalum pentaalkoxide has no more than four carbon atoms and most preferably it is straight chained. The preferred tantalum pentaryloxides are the pentaphenoxide, penta p-chlorophenoxide, and penta p-methyl phenoxide with the phenoxide, the most preferred. A phosphinic acid is the other reactant. The preferred phosphinic acids are represented by the formula RR'P(O)OH wherein R and R' may be

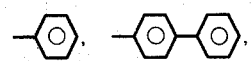

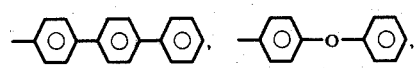

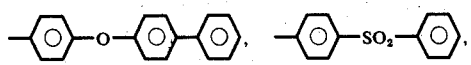

and mixtures thereof. In order to demonstrate the preceding method of preparation the following examples are given. It is to be understood the examples are given by way of illustration and are not meant to limit the specification or the claims to follow.

EXAMPLE I

TaCl$_5$; R and R' = C$_6$H$_5$; Z = Cl

A solution containing 10.0 g of TaCl$_5$ (0.028 mole) and 12.22 g of (C$_6$H$_5$)$_2$P(O)CH (0.056 mole) in 250 ml of benzene was refluxed under nitrogen for five hours. The solvent was then distilled off and the residue was heated in vacuo to 100° C for three hours. Yield, 20.2 g of yellow product, soluble in benzene and chloroform. The properties of this material are indicative of the formulation [Ta(OP(C$_6$H$_5$)$_2$O)$_2$Cl$_3$]$_n$.

EXAMPLE II

X = Cl; R = C$_6$H$_5$;

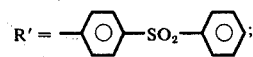

Z = Cl

A solution containing 1.509 g TaCl$_5$ (0.00421 mole) and

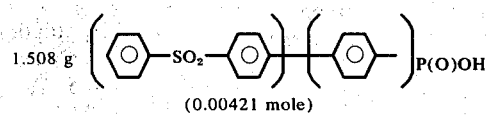

(0.00421 mole)

in 125 ml of benzene was for one hour under nitrogen. The solvent was then distilled off and the residue was heated in vacuo for three hours at 100°. The infrared spectrum and analysis of this product is consistent with the formulation:

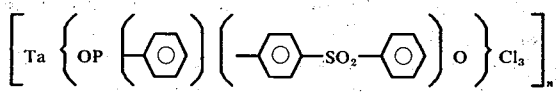

EXAMPLE III

X = OCH₃; R and R' = C₆H₅; Z = OCH₃

Compositions of general formula Ta[OP(C₆H₅)₂O]$_x$-(OCH₃)$_{5-x}$, ($x$= 1, 2, 3), have been prepared by reaction of Ta(OCH₃)₅ with the theoretical amount of (C₆H₅)₂P(O)OH in benzene under nitrogen. The reaction solutions were refluxed for several hours, and then most of the solvent was distilled off. The residual solvent was removed at room temperature under vaccum, and the reaction products were dried at 100° C, also under vacuum. In the case of the tris(phosphinate) derivative the reaction was not complete at this point. Consequently, the residue was redissolved in toluene, and the resulting solution distilled to dryness. The new residue was dried under vacuum at 140° C. All of the methoxides are readily attacked by moisture, and many were found to be partially hydrolyzed when analyzed.

If a tantalum penta halide is used as a reactant, the addition of ammonia in the amount of phosphinic acid decreases the reaction time and increases the yield. This reaction is illustrated as follows:

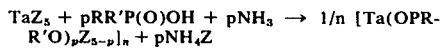

The alkoxy and aryloxy phosphinates may also be prepared by reacting a halide phosphinate with an alcohol. This method is illustrated but not limited by the following examples.

EXAMPLE IV

TaCl₅; R and R' = C₆H₅; Z = OC₂H₅

Tantalum (V) pentachloride (0.0158 mole, 5.672 g) and diphenylphosphinic acid (0.0316 mole, 6.8949 g) were dissolved in 150 ml of benzene (dried over molecular sieves) in a dry nitrogen atmosphere. A fritted glass sparging tube was then immersed in the solution and ammonia gas was passed through for one hour. The solution was then treated with 5 ml of ethanol and it was refluxed for one hour. It was then distilled for two hours with replacement of the benzene when the volume was low. The solution was then filtered under nitrogen and the filtrate was distilled to dryness. The yellow residue was dried in vacuo for two hours. Yield 8.0 g. The product softens around 100° C and is soluble in a variety of organic solvents. Its infrared spectrum and analysis are consistent with the formulation [Ta(OP(C₆H₅)₂O)₂(OC₂H₅)₃]$_n$. Anal. Calcd. for C₃₀H₃₅O₇P₂Ta: C, 48.01; H, 4.70; P, 8.25; Ta, 24.11. Found: C, 47.69; H, 4.36; P, 8.13; Ta, 24.3.

EXAMPLE V

TaCl₅;

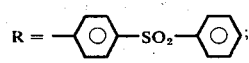

R' = C₆H₅; Z = C₃H₇

A solution containing 1.509 g TaCl₅ (0.00421 mole) and

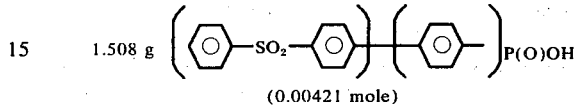

(0.00421 mole)

in 125 ml of benzene was refluxed for one hour under nitrogen. The solution was then treated with 25 ml of isopropanol and refluxed for an additional two hours. It was then treated with ammonia while refluxing an additional hour. The ammonium chloride by-product was filtered off under nitrogen and the solvent was completely removed by heating with an oil bath at 100° C. Yield, 3.0 g of light yellow, soluble residue. The infrared spectrum and analysis of this product is consistent with the formulation:

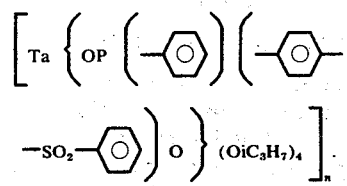

EXAMPLE VI

TaCl₅;

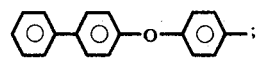

Z = OCH₃

Using the same procedure as in the previous example 1.828 g TaCl₅ (0.0051 mole) was reacted with

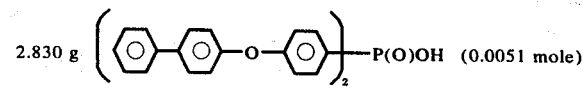

and 40 ml of methanol to give 4.1 g product. The light yellow product is soluble and its analysis and infrared spectrum is consistent with

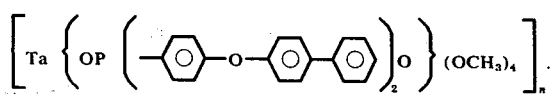

The preparation of all of the reactants is well known except for phenyl sulfonyl phenyl phosphinic acids. The following two examples illustrate the method to be used in their preparation.

EXAMPLE VII

Phenyl[4-(phenylsulfonyl)phenyl]phosphinic acid.

This acid was synthesized in a relatively good yield by the reaction of 4-(phenylsulfonyl)benzenediazonium tetrafluoroborate and dichlorophenylphosphine with copper (I) chloride as a catalyst. The tetrafluoroborate was obtained by the preparation first of 4-nitrophenyl phenyl sulfide from thiophenol and 4-chloronitrobenzene. The sulfide was oxidized with potassium permanganate to the corresponding sulfone and then reduced to 4-aminophenyl phenyl sulfone. The diazonium salt was then prepared as follows. A solution of 26.4 g (0.38 mole) of sodium nitrite in 50 ml of water was added slowly to a slurry of 65.2 g (0.28 mole) of 4-aminophenyl phenyl sulfone in 48% tetrafluoroboric acid while the temperature was maintained in the 0–10° C range with external cooling. The precipitate was collected by filtration, washed with cold aqueous tetrafluoroboric acid, then cold ethanol, and finally ether to give 82.7 g (89%) of product, m.p. 116°–123° C (dec). No attempt was made to obtain an elemental analysis of this unstable intermediate.

To a slurry of 44 g (0.13 mole) of 4-(phenylsulfonyl)benzenediazonium tetrafluoroborate in 400 ml of ethyl acetate was added 22.8 ml (0.17 mole) of dichlorophenylphosphine and 0.5 g of copper (I) chloride. After the reaction had been stirred for two hours at room temperature with no apparent change, it was heated to 30° C (this reaction can be vigorous and care should be used). Evolution of gas occurred, and the solid dissolved. Heating was continued for 1.5 hr., the mixture was then cooled, and 125 ml of water was added. The ethyl acetate and volatile by-products were removed by steam distillation, and then the aqueous residue was cooled and filtered to give a solid that, while still wet, was dissolved in approximately 2 liters of dilute sodium hydroxide. The resulting solution was filtered to remove insoluble non-acidic material and acidified with hydrochloric acid to give 36 g (80%) of crude product, m.p. 220°–4° C. This material was crystallized from 80% ethanol to give 20 g (45%) of phenyl[4-(phenylsulfonyl)phenyl]phosphinic acid. m.p. 225°–8° C. Anal. Calcd. for $C_{18}H_{15}O_4PS$: C, 60.3; H, 4.23; P, 8.64; S, 8.95. Found: C, 60.2; H, 4.49; P, 8.77; S, 9.49.

EXAMPLE VIII

Bis[4-(phenylsulfonyl)phenyl]phosphinic acid

A solution of 30 g (0.1 mole) of 4-bromophenyl phenyl sulfone in 500 ml of THF was cooled to −100° C in a liquid nitrogen-toluene slush, and 42 ml (0.1 mole) of 2.38 M butyl lithium in hexane was added. After about 10 min, 9.5 g (0.05 mole) of $Et_2NPOCl_2$ was added, and the reaction mixture was allowed to warm slowly to room temperature. After 18 hr at room temperature, 125 ml of 6 M HCL was added, and the reaction was heated under reflux for 4 hr. THF was removed by distillation, and 7.5 g of almost white solid, m.p. 115°–130° C, was collected by filtration. This solid was recrystallized from THF to give 7 g (28%) of product, m.p. 155°–165° C. Anal. Calcd. for $C_{24}H_{19}O_6PS_2$: C, 57.8; P, 6.21; S, 12.86. Found: C, 58.5; H, 4.55; P, 6.02; S, 13.06.

This reaction was repeated using a greater ratio of the bromide to $Et_2NPOCl_2$ without significant increase in yield.

Hydrated oxides of general formula $Ta[OPRR'O]_x\cdot O_y\cdot zH_2O$ with different ratios of ligands and water content, have been prepared by suspending the appropriate tantalum phosphinate in boiling water for about 0.5 hr., filtering off the hydrolyzed product, and then drying it under vacuum at 100° C for several hours. The chlorides used for the hydrolysis were prepared from $TaCl_5$ and the theoretical amount of $(C_6H_5)_2P(O)OH$ in benzene under nitrogen.

Deuteration was accomplished by addition of excess $D_2O$ to benzene solutions of $Ta[OP(C_6H_5)_2O]_2O_{3/2}\cdot\frac{1}{2}\lambda H_2O$. After the solution was shaken for 2hr., it was evaporated under nitrogen.

The experimental and analytical results are given in Table I. The calculated values are in parenthesis.

The elemental analysis for all of the examples were run by standard methods. Infrared spectra were recorded with a Perkin Elmer 337 grating spectrophotometer on either Nujol or hexachlorobutadiene mulls between KBr discs. Molecular weight data in benzene and chloroform were obtained at various concentration with a Mechrolab Model 301A vapor pressure osmometer. Thermogravimetric analyses were recorded on a DuPont 950 thermogravimetric analyzer. A Bendix Time of Flight (model 12) mass spectrometer was used to determine the decomposition products. The X-ray powder patterns were obtained with a General Electric XRD-5 X-ray diffraction unit fitted with a Cu source.

Table I

| Example | Sample | Elemental Analysis | | | M.P. |
|---|---|---|---|---|---|
| | | %C | %H | %Ta | |
| IX | $Ta[OP(C_6H_5)_2O]O_2\cdot H_2O^a$ | 32.41 | 2.10 | 39.9 | $N^d$ |
| | | (32.16 | 2.70 | 40.4) | |
| X | $Ta[OP(C_6H_5)_2O]_2O_{3/2}\cdot 3/2H_2O^b$ | 43.51 | 3.29 | 26.29 | 260 |
| | | (43.26 | 3.48 | 27.16) | |
| XI | $Ta[OP(C_6H_5)_2O]_2 O_{3/2}\cdot 1/2H_2O^c$ | 44.16 | 3.53 | 27.57 | 270 |
| | | (44.46 | 3.27 | 27.90) | |
| XII | $Ta[OP(C_6H_5)_2O]_2O_{3/2}{}^c$ | 44.60 | 3.49 | 28.55 | 270 |
| | | (45.09 | 3.15 | 28.30) | |
| XIII | $Ta[OP(C_6H_5)_2O]_3O\cdot H_2O^b$ | 50.09 | 4.05 | 20.85 | 135 |
| | | (49.90 | 3.72 | 20.88) | |

[a]Prepared from corresponding methoxide by hydrolysis.
[b]Prepared from corresponding chloride by hydrolysis.
[c]Prepared from corresponding ethoxide by hydrolysis.
[d]N, no softening point observed up to 350° C.

The analytical results for phosphorus (analyzed colorimetrically after wet digestion) for some of these compounds were very erratic. Further experiments showed that tantalum interferes — probably because of the formation of a strong phosphate tantalum complex. For this reason, phosphorus analyses are not reported.

In summary the preferred tantalum phosphinates are: $[Ta(OPRR'O)_pZ_{(5-p)}]_n$ wherein $1 \leq p \leq 3$; $n$ any number; $Z = Cl, Br, OCH_3, OC_2H_5, OC_3H_7, OC_4H_9,$ $OC_6H_5, OC_6H_4Cl,$ or $OC_6H_4CH_3$;

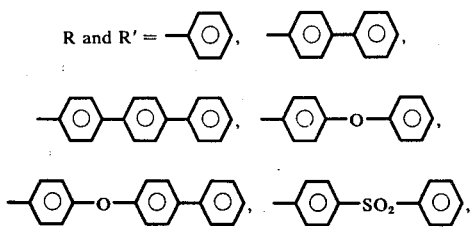

or mixtures thereof. The preferred hydrated oxides of the tantalum phosphinates of this invention are: $[Ta[OPRR'O]_xO_y\cdot zH_2O]_n$ wherein $1 \leq x \leq 3$, $y = (5-x/2)$, $0.5 \leq z \leq 2.0$, $n$ is any value, and R and R' are as before.

To demonstrate the utility of the compounds of this invention the following examples are given by way of illustration and not by way of limitation.

EXAMPLE XIV

A m-cresol solution containing amounts of weight of $\{Ta[OP(C_6H_5)_2O]_2(OH)_3\}_n$ and poly(phenylquinoxaline) (PPQ 401 produced by Whittaker Corp.) was applied by brush to CCA-1 carbon cloth. The impregnated cloth was placed in forced air oven at 120° F for 8 min to remove some m-cresol and then precured at 180° F for 60 min, at 200° F for 40 min and finally at 250° F for 30 min. The prepeg was cut into the desired size and the stacked plies (12) were kept under contact pressure in a hydraulic press while the platens were heated from room temperature of 750° F. Full pressure was applied at 750° F for 4 hrs. The flexural strengths of the laminates pressed under 1500 and 2000 psi were 28,100 and 32,000 psi, respectively.

EXAMPLE XV

A solution containing equal weights of $\{Ta[OP(C_6H_5)_2O]_2\text{-}(OC_2H_5)_3\}_n$ and P13N polyimide precursor in DMF was applied on E-glass cloth 181 with 112 finish. The coated cloth was cut into the desired size and precured at 320° F for 4 min. Finally, it was pressed at 600° F under 800 psi for 60 min. The flexural strengths of the laminates ranged from 78,000 to 92,000 psi.

Obviously many modifications and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. A poly[tantalum phosphinate] of the general formula: $[Ta(OPRR'O)_pZ_{5-p}]_n$ wherein $1 \leq p \leq 3$; $n$ is any number; $Z = Cl, Br, OCH_3, OC_2H_5, OC_3H_7, OC_4H_9, OC_6H_5, OC_6H_4Cl, OC_6H_4CH_3$ or mixtures thereof; R and $R' = C_6H_5$, $(C_6H_4)(C_6H_5)$, $(C_6H_4)(C_6H_4)(C_6H_5)$, $(C_6H_4)\text{-}O\text{-}(C_6H_5)$, $(C_6H_5)(C_6H_4)\text{-}O\text{-}(C_6H_4)$, $(C_6H_4)\text{-}SO_2\text{-}(C_6H_5)$, or mixtures thereof.

2. The poly[tantalum phosphinate] of claim 1 wherein $R = C_6H_5$ and $R' = C_6H_5$, $(C_6H_4)(C_6H_5)$, $(C_6H_4)(C_6H_4)(C_6H_5)$, $(C_6H_4)\text{-}O\text{-}(C_6H_5)$, $(C_6H_4)\text{-}O\text{-}(C_6H_4)(C_6H_5)$, or $(C_6H_4)\text{-}SO_2\text{-}(C_6H_5)$.

3. The poly[tantalum phosphinate] of claim 1 wherein R and $R' = (C_6H_5)$, $(C_6H_4)(C_6H_5)$, $(C_6H_4)(C_6H_4)(C_6H_5)$, or mixtures thereof.

4. The poly[tantalum phosphinate] of claim 1 wherein R and $R' = (C_6H_4)\text{-}O\text{-}(C_6H_5)$, $(C_6H_5)(C_6H_4)\text{-}O\text{-}(C_6H_4)$, or mixtures thereof.

5. Oxide hydrates of the poly[tantalum phosphinates] of claim 1 having a general formula of $[Ta[OPRR'O]_xO_y\cdot zH_2O]_n$ wherein $1 \leq x \leq 3$, $y = (5-x/2)$, and $0.5 \leq z \leq 2.0$.

* * * * *